United States Patent [19]

Oosterwijk et al.

[11] 4,036,898

[45] July 19, 1977

[54] NOVEL CHLORINATED DICUMENE INITIATORS

[75] Inventors: Hendrik H. J. Oosterwijk, Diepenveen; Eduard P. Magré, Wiersum; Wilhelmus M. Beyleveld, Olst, all of Netherlands

[73] Assignee: Akzona Incorporated, Asheville, N.C.

[21] Appl. No.: 621,985

[22] Filed: Oct. 14, 1975

[30] Foreign Application Priority Data

Oct. 14, 1974  Netherlands .......................... 7413633

[51] Int. Cl.$^2$ ............................................. C07C 25/22
[52] U.S. Cl. ................................... 260/649 R; 526/89

[58] Field of Search ..................................... 260/649 R

[56] References Cited

FOREIGN PATENT DOCUMENTS 238,143   10/1945   Switzerland ..................... 260/649 R

*Primary Examiner*—C. Davis
*Attorney, Agent, or Firm*—Francis W. Young; Robert F. Green

[57] ABSTRACT

This invention relates to aliphatically chlorinated dicumene derivatives useful as photoinitiators in the polymerization of ethylenically unsaturated monomers such as styrene, ethylene and acrylic acid.

1 Claim, No Drawings

NOVEL CHLORINATED DICUMENE INITIATORS

BACKGROUND OF THE INVENTION

Many reactions carried out in chemical technology proceed under the influence of radicals, the formation of which can proceed in various ways.

Thus, chlorination of the lateral chain of toluene —a well-known substitution reaction —may proceed under the influence of light, as well as of a chemical radical initiator, such as radicals formed from peroxide. Another example is the polymerization of styrene, which can be carried out under the influence of heat, as well as with the aid of a peroxide. In general, the higher reaction rate obtainable therewith is an advantage of the use of a chemical radical initiator. Among other things, a disadvantage may be by-products liberated during its degradation. Although the quantity of radical initiator used is in general very small, the concentration of formed by-products is frequently still so high, that the presence thereof in the end product may even harmful to its quality. The latter may also occur in the case of polymers formed under the influence of radicals; the removal of by-products from these is frequently not possible.

Use of a purely thermal polycondensation is afflicted with the drawback of a long duration, which is necessary to obtain an adequately high degree of polymerization. In order to meet this drawback, radical initiators have indeed been proposed, which being to develop their activity only at elevated temperatures, e.g., between 150° and 250° C. Below this temperature, these initiators are practically stable, so that they are not used up during the "main polymerization" under the influence of heat and therefore may be added to the reaction mixture already at the beginning of polymerization. An important advantage of this characteristic is the fact that only very little of these initiators needs to be added to the mixture to be polymerized, since they only have the function to accelerate the progress of "afterpolymerization," at the beginning of which mostly not more than about 5% of the initial quantity of monomer is present.

Examples of such radical formers, to which belong, among others, certain 1,2- diaryl-1,1,2,2,-tetraalkylethane compounds, are mentioned in British Pat. No. 864,675. In this patent, preference is given to 1,2-diaryl-1,1,2,2-tetraalkylethane compounds in which at least one alkyl group with more than one C atoms is bonded to each of the two C atoms of the ethane group. As an example, mention is mad of (α-methyl α-ethyl- β-methyl-βethyl)-diphenylethane (=3,4,- diphenyl-3,4- dimethylhexane). The last-mentioned type of compound appears to be very suitable for the application in question.

However, a drawback of these compounds is their high price. The reason is, that their preparation starts with the relatively high expensive secondary butylbenzene, which is dimerized in a manner analogous to cumene. The dimerization product of the last-mentioned substance is dicumyl (or dicumene), which can be considered the simplest representative of the mentioned tetraalkylethane compounds. The price of cumene is relatively low, but the initiator activity of the dimer appears to be insufficient for practical applications.

THE INVENTION

Surprisingly, new radical-forming compounds have been found which compare favorably with the mentioned 3,4- diphenyl- 3,4-dimethylhexane and which are furthermore very easily accessible by means of synthesis.

The compounds of the invention have the general formula:

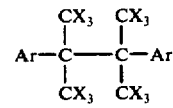

wherein Ar represents an aryl group and X a chlorine or hydrogen atom, with the understanding that at least one X and at most 5 X per molecule are chlorine atoms.

In the formula given above, Ar represents an aromatic group (substituted or unsubstituted), such as a phenyl, biphenyl, naphthyl, thienyl or anthracyl groups. Preferably, Ar is an unsubstituted phenyl group. this means, that for the preparation of the preferred compound pursuant to the invention it is possible to start out with cumene, which is commercially available in great quantities. Starting with cumene, dicumene (also called "dicumyl") can be prepared by several known methods. For example, in U.S. pat. No. 3,384,658 cumene and diphenyl carbonyl are subjected to ultraviolet radiation (2000 –4000 angstroms). U.S. Pat. Np. 3,621,069 uses cumene hydroperoxide to dimerize cumene at elevated temperatures (e.g., 215° C.) and pressures (75 psi). German pat. No. 2,342,185 describes cumene dimerization using peroxy ethyl phosphonate as a catalyst. The above patents are incorporated into the present application by reference to the extend they further describe the cumene dimerization.

The new compounds pursuant to the above formula can be obtained by reacting a compound with the above formula, wherein X =H, dissolved in an organic solvent, with chlorine in the presence of a catalytic quantity of iodine and/or radiation with ultraviolet light, followed by isolation of the resulting compound. The reaction utilizes any of the solvents commonly employed in chlorination reactions such as benzene, CCl$_4$, CHCl$_3$, CH$_2$Cl$_2$, dimethyl formamide, and the halobenzenes. Other parameters of the chlorination reaction, such as the quantity of iodine to be added or the dosage level or radiation, correspond with conventional chlorination reactions and can readily be determined by routine experimentation.

Another attractive method for the preparation of the new compounds pursuant to the invention consists in reacting a compound with the above formula, dissolved in an organic solvent, wherein X = H, sulfuryl chloride in the presence of an organic peroxide, followed by isolating the resulting compound. For the organic peroxide, use is preferably made of an acyl peroxide, such as benzoyl peroxide, but other peroxides may also be considered. Isolating and purifying of the compounds pursuant to this invention is preferably carried out by means of evaporation of the solvent and of oeht volatile components that may be present.

The invention also refers to a method for the execution of chemical reactions initiated by radicals under the influence of the new compounds pursuant to the invention. Here, perference is mainly given to compounds with at most two chlorine atoms in the aliphatic chains located between the aryl groups, i.e., 2X groups in the above formula.

In addition, the invention refers to a method for the execution of a polymerization reaction initiated by radicals by incorporating a catalytic quantity of a compound with the formula given above in an ethylenically-unsaturated monomer or prepolymer mainly containing an aromatic vinyl group, an allyl compound or ethylene, and heating of the mixture towards the end of the polymerization reaction to a temperature between 150° and 250° C.

Within the framework of the invention, a monomer or prepolymer containing mainly an aromatic vinyl group, an allyl compound or ethylene means that the polymer compositions contain at least 50% by weight of one or several of the mentioned compounds.

Among others, an aromatic vinyl group is understood to mean styrene and divinyl benzene. The method pursuant to the invention can likewise be applied in the preparation of so-called impact-resistant polystyrene compounded on the basis of styrene and perhaps other monomers, and finely distributed rubber-like polymers. Diallyl phthalate and diallyl carbonate can be mentioned as examples of allyl compounds to be (after) polymerized making use of the new compounds pursuant to the invention.

As already explained above, only very small quantities of the radial initiators in question need to be incorporated. Depending upon the intended application, this quantity will in practice vary between 0.001 and 0.5% by weight, calculated on the basis of the weight of the polymerizable material.

Preferably, use is made of a quantity between 0.01 and 0.1% by weight.

In addition to the application as radical initiator for chemicl reactions and polymerization reactions, which was stated above, it has been found that the new compounds involved here are very suitably for application as synergistic substances in compositions containing flame-resistant, organic, brominated compounds. In general, it is then necessary to incorporate more of the compounds in question in the polymers to be made flame-resistant. The figure may vary from 0.01 to 5% by weight, calculated on the basis of the polymer. In general, the bromine will be aliphatically bonded in the bromine compound, while the quantity of bromine compound to be taken up is as a rule selected in such a way that the masses do not contain more than 5% by weight of bromine.

Preferably, the percentage of bromine amounts to 0.5 to 3% by weight, calculate on the base of the polymer.

Application as a flame extinguisher is mainly of interest in polystyrene and copolymers thereof, whereby at least 50 % by weight of the styrene monomer is incorporated in the latter. In addition, application as flame extinguisher is also of interest in polypropylene, polymethacrylate and copolymers of the latter.

In addition to the advantages already listed above, application of the compounds in question as radical initiators also offers advantages compared with the very frequently used peroxides. The reason is, that the compounds in question have a much more specific effect and do not give rise to undersirable side reactions, such as the formation of undersirable cross-links, in view of the fact that at low temperatures they may be left in the reaction mixture for a long time without the occurrence of any reaction, they are eminently suited for application in stable, moldable compositions, the polymerization of which can be restarted at a given moment by means of heating. A known example of such compositions are unsaturated polyester resins.

Another advantage of using the compounds in question is that, in contrast to the frequently used azodinitriles or peroxides, they do not give rise to gas development which is not permissible in a number of reactions initiated by radicals, nor to any compounds with an unpleasant odor.

In the method pursuant to the invention, compositions of radical-formers and polymerizable compounds, such as monomers, prepolymers, or polymers, which may also be provided with cross-links, can be given the desired shape and hardened by heating.

Here, polymerizing in the widest sense is meant by hardening, which means that it does not necessarily have to go hand in hand with the formation of cross-links. Giving the compositions of radical-formers and polymerizable compounds the desired shape may, e.g., consist of the application of covering layers, casting in molds, application of the composition to glass fiber structures or other reinforcements, impregnating of all kinds of materials, injection molding, extruding, vacuum forming, of of some other shaping technology.

Application of the method pursuant to the invention opens the door to the possiblity of performing polymerization reactions in several stages. Thus, it is e.g. possible to mix a monomer with the radical-former(s) pursuant to the invention and to initiate polymerization by means of heating. After the polymerization reaction has been partly completed, it is possible to interrupt the reaction by lowering of the temperature. In that case, one will have a mixture of monomer and polymer (here also referred to as prepolymer), which later on, after it has been shaped, can be polymerized further. If desired, it is of course possible to add compounds before further polymerization, which compounds will have the result that cross-links will be formed during further polymerizaion.

In general, one will proceed in such a way that at first a polymerization reaction is carried out pursuant to commonly employed techniques to form a prepolymer. Thus, it is possible to let the monomer or monomer mixture polymerize as such. Polymerization can also be allowed to take place in a solution, in a suspension or in an emulsion. In order to complete the polymerization or to form cross-links, the prepolymer is subsequently heated to a temperature between 150 and 250° C., as a result of which the radical initiator pursuant to the invention will be activated and the hardening process can begin.

Preferably, the radical initiators pursuant to the invention are incorporated in the monomer mixture already before formation of the prepolymer, if desired, simultaneously with customary auxiliary substances.

The invention will now be illustrated by a number of examples. It is of course understood that these examples are intended for illustration of the invention. Other such examples will be readily apparent to one skilled in the art.

EXAMPLE I

PREPARATION OF MONO- AND DICHLORODICUMYL 47 grams of dicumyl were placed in a 3-necked flask equipped with an agitator, a thermometer and a reflux cooler. 108 g. of sulfuryl chloride in 200 ml. of benzene were added thereto, whereupon 1.0 g. benzoyl peroxide was added while nitrogen was passed through.

The mixture, which was agitated continuously, was heated to 75°—80° C. for 1½ hours with reflux cooling, whereupon the excesses of sulfuryl chloride and benzene were removed at a reduced pressure. This resulted in 60 g. of raw product, which was treated with petroleum ether. An insoluble, solid fraction of 38 g. with a melting range from 100° to 160° C. was obtained thereby. The soluble, viscous fraction amounted to 21 g.

The chlorine content of both fractions amounted to 15.4 and 24.7 % by weight, respectively (theoretical values for the mono- and dichloro compounds were 13.0 and 23.1% by weight).

It was possible to determine by means of infrared spectroscopy that the chlorine was exclusively located in the aliphatic chains.

EXAMPLE II

PREPARATION OF PENTACHLORODICUMYL

A quantity of 16.7 g. dicumyl dissolved in 100 ml. carbon tetrachloride was placed in a 3- necked flask equipped with agitator, thermometer and reflux cooler. A few grains of iodine were added thereto, whereupon 25 g. of chlorine gas were introduced at 20° C. during 2¼ hours with agitation. The reaction mixture was washed with, one after the other, 1 N soda lye solution, a 10% by weight solution of sodium sulfite in water and finally with pure water, until no basic reaction could be observed with litmus paper. 27.4 g. of product were left after removal of the solvent.

It consisted of a highly viscous liquid with a chlorine content of 42.2% by weight. This corresponds to the composition of pentachlorodicumyl.

EXAMPLE III 100 ml. of styrene were distilled under nitrogen and divided into 10 parts. A quantity of radical initiator of 0.05% by weight, calculated on the basis of the monomer quantity, was added to each part.

One g. of monomer of each of these parts was transferred to glass ampoules with a content of approximately 3 ml. Before the ampoules were sealed by melting, the contents were cooled in solid $CO_2$ under a stream of $N_2$. Subsequently, the ampoules were exposed to the following temperatures pursuant to the schedule listed below:

| Time (hr.) | Temperature ° C. |
|---|---|
| 7 | 110 |
| 5 | 130 |
| 5 | 150 |
| 5 | 170 |
| 5 | 190 |

After heating at these temperatures has been terminated, one ampoule after the other was checked for unreacted monomer. The results of the investigation are listed in the following table:

TABLE 1

| Experiment Number | Radical Initiator 0.05% by Weight | Remaining Monomer in % after Heating at 170° C. | Remaining Monomer in % after Heating at 190° C. |
|---|---|---|---|
| 1 | none (control) | 2.1 | 1.05 |
| 2 | dicumyl | 1.41 | 0.70 |
| 3 | 3,4-diphenyl-3,4 dimethylhexane | 0.77 | 0.03 |
| 4 | monochlorodicumyl (aliphatic chlorination) | 0.94 | 0.03 |
| 5 | dichlorodicumyl (aliphatic chlorination) | 0.70 | 0.02 |
| 6 | dichlorodicumyl (aromatic chlorination) | 2.5 | 1.3 |

The above Table shows clearly, that among the investigated compounds, dicumyl and dicumyl chlorinated in the aromatic nucleus do not meet requirements because of too high a residual monomer content after heating at 190° C. Only the initiator activity of 3,4- diphenyl- 3,4- dimethylhexane, known from British Pat. No. 864,675, can be compared with the compound pursuant to the invention in question, but, due to the difficulty accessibility of the initial product, it is not very attractive for commercial applications.

WHAT IS CLAIMED IS:

1. An aliphatically chlorinated cumene dimer corresponding to the formula:

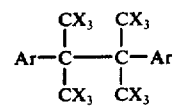

wherein Ar is an aryl group and X is hydrogen or chlorine and provided that at least 1 but not more than 5 X groups are chlorine.

* * * * *